(12) United States Patent
Kikuchi et al.

(10) Patent No.: US 6,773,392 B2
(45) Date of Patent: Aug. 10, 2004

(54) ENDOSCOPE

(75) Inventors: Akira Kikuchi, Yokohama (JP); Masakazu Higuma, Nirasaki (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/085,739

(22) Filed: Feb. 28, 2002

(65) Prior Publication Data
US 2002/0128535 A1 Sep. 12, 2002

(30) Foreign Application Priority Data

Mar. 12, 2001 (JP) ........................................ 2001-069104
Jan. 25, 2002 (JP) ........................................ 2002-017315

(51) Int. Cl.⁷ ................................................ A61B 1/04
(52) U.S. Cl. ........................ 600/109; 600/129; 600/130; 600/160
(58) Field of Search ................................ 600/109, 129, 600/130, 160, 176, 181

(56) References Cited

U.S. PATENT DOCUMENTS

| 4,841,952 A | * | 6/1989 | Sato et al. ........................ 128/6 |
| 4,905,082 A | * | 2/1990 | Nishigaki et al. ............. 358/98 |
| 5,018,832 A | * | 5/1991 | Terunuma et al. .......... 350/276 |
| 5,078,773 A | * | 1/1992 | Thomas ........................... 65/37 |
| 5,235,965 A | * | 8/1993 | Hiroya ............................ 128/6 |
| 5,454,366 A | * | 10/1995 | Ito et al. ...................... 600/109 |
| 5,601,525 A | * | 2/1997 | Okada ......................... 600/160 |
| 5,980,454 A | * | 11/1999 | Broome ....................... 600/176 |
| 6,080,101 A | * | 6/2000 | Tatsuno et al. ............. 600/112 |

FOREIGN PATENT DOCUMENTS

| JP | 2000-107120 | 4/2000 |
| JP | 2000-342512 | 12/2000 |

* cited by examiner

Primary Examiner—John P. Leubecker
Assistant Examiner—Aaron Roane
(74) Attorney, Agent, or Firm—Scully, Scott, Murphy & Presser

(57) ABSTRACT

An endoscope includes a first lens barrel having a brazing surface in at least a brazing portion thereof, and supporting an optical window member brazed thereon, and a second lens barrel arranged to be proximal with respect to the optical window member and supporting optical members on the inner circumference thereof. At least a distal end surface of one of the second lens barrel, a diaphragm member, a spacer ring, and the optical members has light reflectance lower than that of the brazing surface of the first lens barrel. At least the inner circumference of the second lens barrel has a light reflectance lower than that of the brazing surface of the first lens barrel or has a reflection surface more irregular than the brazing surface of the first lens barrel.

11 Claims, 10 Drawing Sheets

ENDOSCOPE

This application claims benefit of Japanese Application No. 2001-069104 filed on Mar. 12, 2001, and No. 2002-017315 filed on Jan. 25, 2002, the contents of which are incorporated by this reference.

BACKGROUND OF THE INVENTION

1. Field of the Invention

The present invention relates to an endoscope and, more particularly, an autoclave sterilization type endoscope.

2. Description of the Related Art

Endoscopes are now widely used in the medical care field. The insert section of the endoscope is inserted into the body cavity of a human to observe a deep portion of the body, and if necessary, a medical treatment is performed using an instrument together with the endoscope.

To control communicable diseases, sterilizing and disinfecting a medical endoscope after use are an essential requirement.

Gaseous disinfectants, such as ethylene oxide, or antiseptic solutions are conventionally used in a sterilization process. As is well known, gaseous disinfectants are highly toxic, and a sterilization process becomes complex to assure safety of humans. Since aeration to evacuate gas residing on an instrument subsequent to the sterilization process takes time, the endoscope cannot be used immediately after the sterilization process. Furthermore, adverse effects of the gas to the environment become a concern. The running cost involved in the sterilization process is high.

The management of the antiseptic solutions is typically complicated, and a great deal of cost is required to dispose the used antiseptic solutions.

In the field of endoscopes, the autoclave sterilization is becoming a mainstream sterilization process because it requires no complex handling procedure, permits use immediately subsequent to the sterilization process, and involves no high running cost. The autoclave sterilization process sterilizes bacteria by infiltrating vapor into the bacteria under a high pressure (of about 0.2 MPa) and a high temperature (within a range of from 120° C. to 135° C.).

However, high-pressure vapor typically penetrates almost all polymeric materials (resin, rubber, resin adhesives, etc). For example, epoxy resin, which is a widely used adhesive agent, permits a high-pressure vapor to penetrate therethrough in the autoclave sterilization process. The epoxy resin under a direct attack by the high-pressure vapor deteriorates and may be cracked. Since the autoclave sterilization process involves a high temperature, a stress is generated between components due to difference in thermal expansion coefficient from material to material. This may be another cause of cracks in the adhesive agent.

In the autoclave sterilization process, vapor penetrates through a connection portion of an optical window, and enter a lens system, thereby clouding the surface of a lens in the lens system. There is a conventionally available technique which air-tight connects the connection portion of an optical window member by soldering or brazing rather than by using an adhesive.

For example, Japanese Unexamined Patent Application Publication No. 2000-342512 discloses a technique in which a lens barrel is subjected to a surface treatment such as gold plating before soldering a distal-end lens as the optical window member. To perform sound brazing, a surface treatment, such as gold plating, nickel plating, or tin plating, needs to be performed on the surface of a component. Such a pre-brazing surface finish is typically glossy. The surface of the lens barrel then becomes reflective. Since light rays are reflected from a flat bottom of a lens brazed to the lens barrel and an inner circumference of a lens barrel of a second lens thereafter, optical problems such as flare are created.

A metal such as brass permits sound brazing without the need for plating. If such a metal is used for the lens barrel, the material itself is glossy, and the same problem is created.

Japanese Unexamined Patent Application Publication No. 2000-107120 discloses a technique in which a lens barrel supporting a lens is fabricated of a ceramic such as aluminum nitride, sialon, alumina, silicon nitride, or silicon carbide. Since the surface of these materials is not sufficiently low in reflectance, the inner diameter of the lens barrel is increased so that no light rays are incident on the inner circumference of the lens barrel. Furthermore, when a ceramic is used for the lens barrel, the thickness of the lens barrel needs to be increased to assure machinability and mechanical strength. Consequently, the image pickup unit of the endoscope becomes bulky in size with an enlarged distal end diameter of the endoscope.

Japanese Unexamined Patent Application Publication No. 2000-107120 discloses a technique in which an optical diaphragm is not arranged immediately proximal to an optical window. In this arrangement, a light ray is reflected from a distal end of a metal-plated lens barrel supporting an optical window member, and is incident on a solid-state image pickup device, thereby resulting in optical problems. To control such optical reflections, the optical window and the distal end barrel need to be enlarged in diameter. A bulky image pickup unit thus results.

SUMMARY OF THE INVENTION

Accordingly, it is an object of the present invention to provide an endoscope with a small diameter distal end wherein the endoscope is free from clouding in a viewing optical system thereof and optical problems such as flare during an autoclave sterilization process.

An endoscope of the present invention in one aspect includes a viewing optical system including a plurality of optical members and an optical window member arranged at a distal end of the viewing optical system, a first lens barrel having a brazing surface in at least a brazing portion thereof, and supporting the optical window member brazed thereon, a second lens barrel arranged to be proximal with respect to the optical window member and supporting the optical member on the inner circumference thereof. At least a distal end surface of one of the second lens barrel, the diaphragm member, the spacer ring, and the optical member has light reflectance lower than that of the brazing surface of the first lens barrel.

An endoscope of the present invention in another aspect includes a viewing optical system including a plurality of optical members and an optical window member arranged at a distal end of the viewing optical system, a first lens barrel having a brazing surface in at least a brazing portion thereof, and supporting the optical window member brazed thereon, and a second lens barrel arranged to be proximal with respect to the optical window member and supporting the optical member on the inner circumference thereof, wherein at least the inner circumference of the second lens barrel has light reflectance lower than that of the brazing surface of the first lens barrel or has a reflection surface more irregular than the brazing surface of the first lens barrel.

The above and other objects, features and advantages of the invention will become more clearly understood from the following description referring to the accompanying drawings.

DESCRIPTION OF THE PREFERRED EMBODIMENTS

Figure 1:
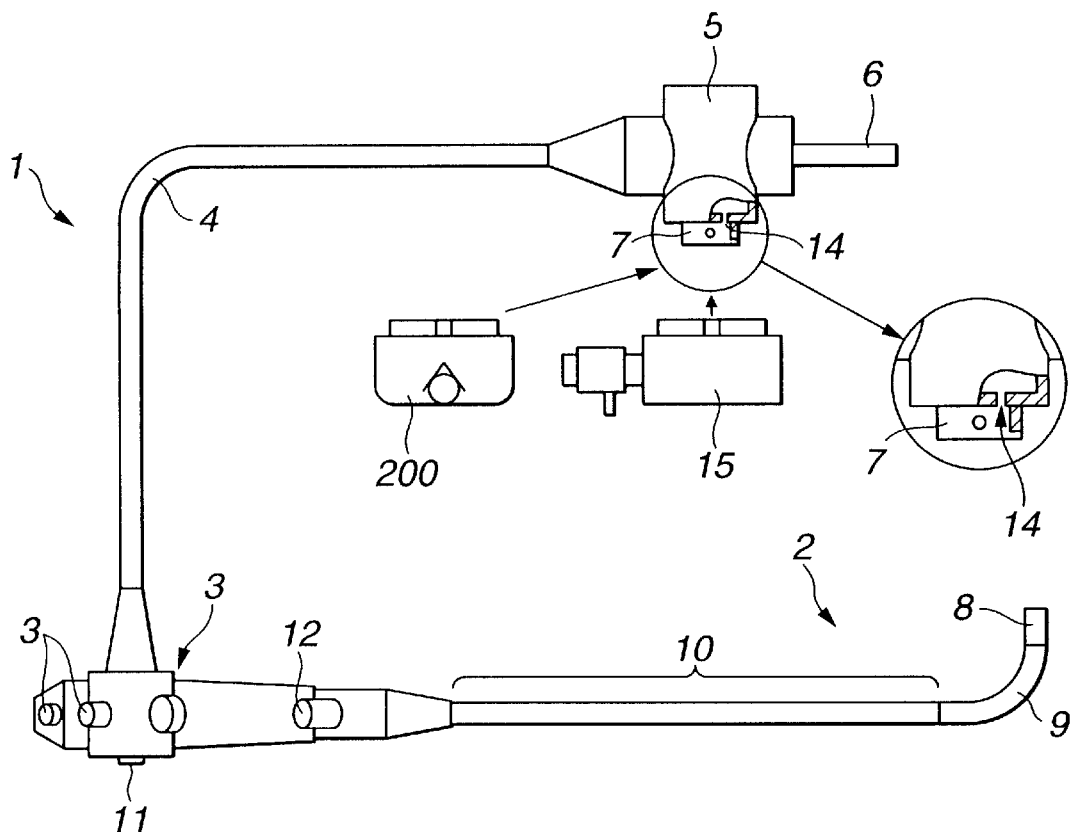
FIG. 1 is a diagram illustrating the construction of an electronic endoscope of the present invention.

Referring to the drawings, the embodiments of the present invention are discussed below.

A first embodiment of the present invention will now be discussed, referring to FIGS. 1 through 4.

Figure 2:
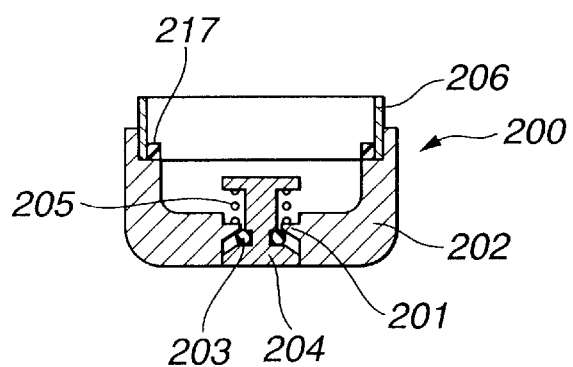
FIG. 2 is a cross-sectional view illustrating a check valve cap.
Figure 3:
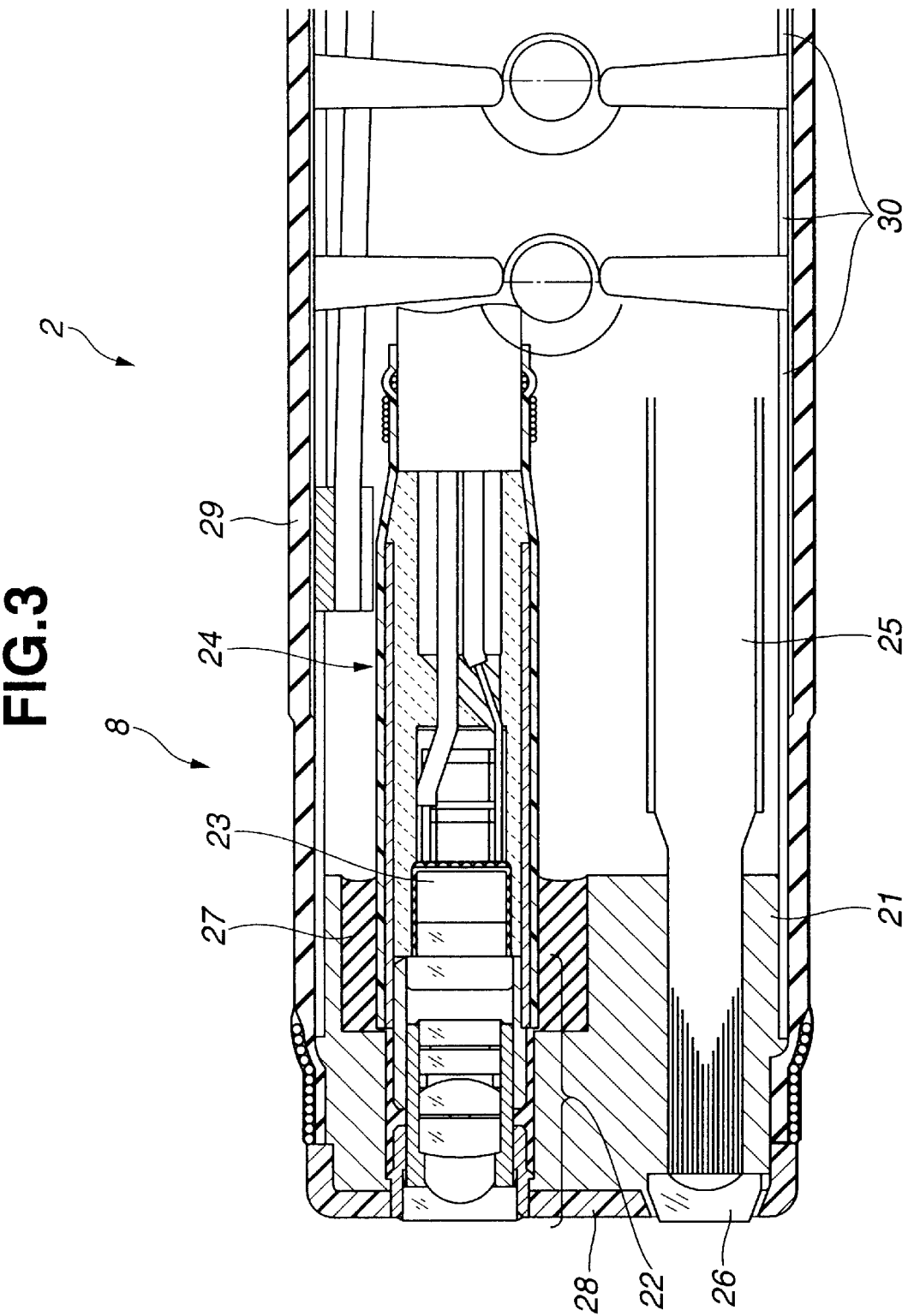
FIG. 3 is a longitudinal sectional view of a distal portion of the electronic endoscope of the present invention.

FIG. 1 is a diagram illustrating the construction of an electronic endoscope 1 of the present invention. FIG. 2 is a cross-sectional view illustrating a check valve cap. FIG. 3 is a longitudinal sectional view of a distal portion of the electronic endoscope 1 of the present invention.

Referring to FIG. 1, the electronic endoscope 1 of this embodiment includes an insert section 2 having a CCD (Charge-Coupled Device) in a distal portion thereof as a solid-state image pickup device, a control section 3 which is connected to a proximal end of the insert section 2 and gripped by an observer to perform a variety of operations, and a universal cord 4 extending from the control section 3. A connector section 5 is attached to the other end of the universal cord 4. The connector section 5 is connected to an optical device (not shown) and a camera control unit (hereinafter referred to as "CCU") (not shown).

A light guide connector 6 is connected to the optical device, and a camera connector 7 is connected to the CCU. The insert section 2, the control section 3, the universal cord 4, and the connector section 5 communicate with each other via the internal space thereof. Specifically, a single endoscopic internal space (also simply referred to as internal space) is formed with the housing of the endoscope.

The insert section 2 includes a distal end portion 8, a bending portion 9 free to bend, and a flexible portion 10 having flexibility. The control section 3 includes a bend control lever 11, which controls the movement of the bending portion 9, an instrument insert port 12 through which an instrument, such as forceps, is inserted, and a plurality of switches 13 for performing an image freeze or release, for example. The bend control lever 11 is free to rotate, and is mounted in a water-tight fashion using an O-ring (not shown).

The camera connector 7 includes a ventilation hole 14 for providing ventilation in the internal space of the endoscope 1. A waterproof cap 15 is detachably mounted on the camera connector 7. With the waterproof cap 15 mounted on the camera connector 7, the internal space of the electronic endoscope 1 is water-tight. When the waterproof cap 15 is removed, the internal space defined by the housing of the electronic endoscope 1 communicates with outside.

The waterproof cap 15 is attached while the electronic endoscope 1 is cleaned after use or while the electronic endoscope 1 is immersed into an agent solution. During the cleaning of the electronic endoscope 1 with running water or the immersion of the electronic endoscope 1 in an agent solution, the waterproof cap 15 closes the camera connector 7 in a watertight manner to prevent any liquid from entering the internal space of the electronic endoscope 1. A check valve cap 200 is detachably connected to the camera connector 7. The check valve cap 200 has a check function that allows a gas to pass outwardly from the internal space of the electronic endoscope 1 while preventing a gas from entering the electronic endoscope 1.

Referring to FIG. 2, the check valve cap 200 includes a check valve cap metal body 202 with a seat ring 201, a metallic valve element 204 or the like integrally arranged with a rubber sealing member 203, a spring 205 for biasing the valve element 204 against the seat ring 201, a metallic socket section 206 mated into the camera connector 7, and a rubber sealing member 217 that maintains watertightness between the inner circumference of the socket section 206 and the outer circumference of the camera connector 7 when the socket section 206 is fitted around the camera connector 7.

Instead of the waterproof cap 15, the check valve cap 200 is mounted to the camera connector 7 when the electronic endoscope 1 is autoclave sterilized. With the check valve cap 200 mounted, a high-pressure and high-temperature vapor is prevented from entering the endoscope 1 through the ventilation hole 14 during the autoclave sterilization process.

The bias force of the spring 205 is set so that the spring 205 biases the valve element 204 against the seat ring 201 to tightly press the sealing member 203 against the seat ring 201 in the normal state, i.e., when the check valve cap 200 is mounted onto the camera connector 7. During a depressurization phase of the autoclave sterilization process, the biasing of the valve element 204 against the seat ring 201 is released.

As long as the internal pressure in the internal space of the endoscope 1 remains lower than the ambient pressure, in other words, during the normal operating condition, the check valve cap 200 keeps the endoscope 1 watertight to the ambient air. While the endoscope 1 is cleaned with water or immersed in an agent solution, the check valve cap 200 instead of the waterproof cap 15 may be mounted.

FIG. 3 illustrates the distal end portion 8 of the insert section 2 in enlargement.

Arranged in a distal end body 21 forming the distal end portion 8 are an objective optical system 22 as a viewing optical system, an image pickup unit 24 having an image pickup device 23 as image pickup means, and a light guide fiber 25 which is a light guide for transmitting an illumination light beam. The image pickup unit 24 is at least partly embedded into the distal end body 21. Referring to FIG. 3, a filler 27 is applied around the image pickup unit 24. This arrangement controls attacking of the image pickup unit 24 by vapor entering the endoscope 1. An illumination lens 26 is mounted on the distal end of the light guide fiber 25.

The distal end body 21 is preferably fabricated of a metal such as stainless steel from the standpoint of mechanical strength and machinability. A distal end cover 28, fabricated of an insulator such as a plastic or a ceramic, covers the distal end of the distal end body 21 so that almost no portion of the metallic distal end body 21 is outwardly exposed. The distal end cover 28 is intended to insulate the distal end portion 8 from outside. A bending rubber 29 is attached around the outer circumference of the distal end body 21, and covers the outer circumferences of a plurality of ring segments 30 arranged behind the distal end body 21. In this arrangement, the outside of the distal end portion 8 is insulated.

Figure 4:
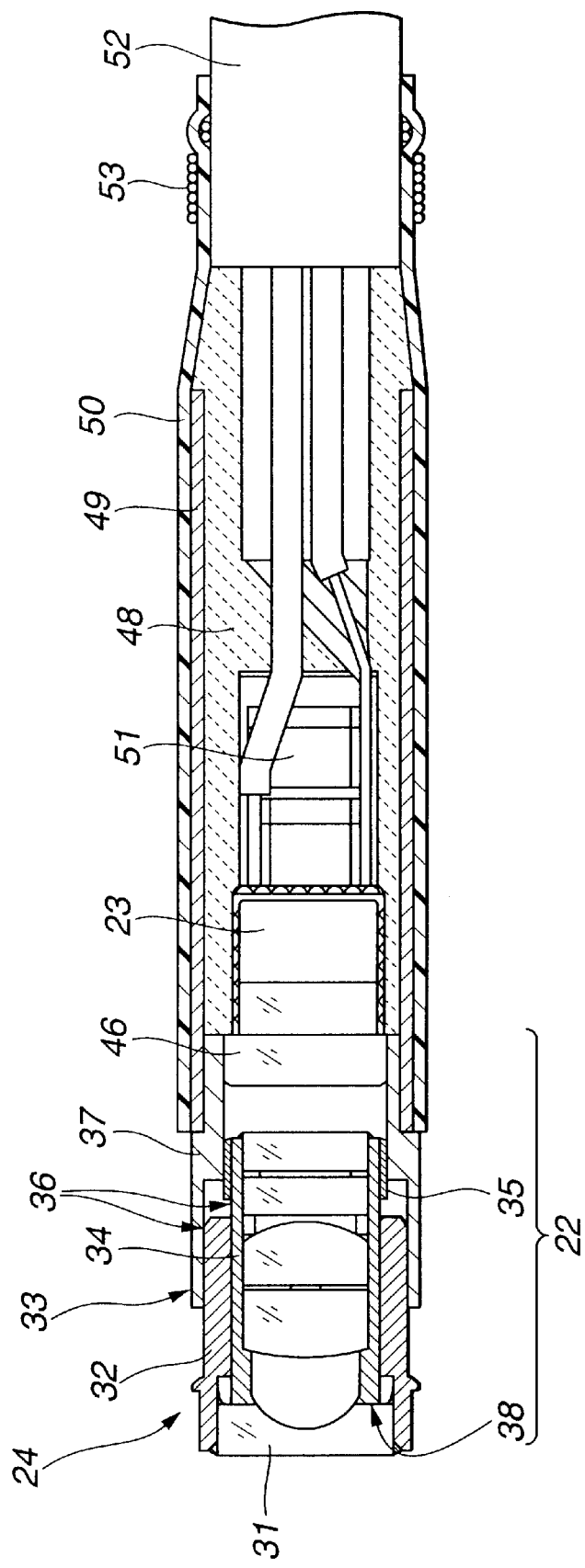
FIG. 4 is a longitudinal sectional view of an image pickup unit in accordance with a first embodiment of the present invention.

FIG. 4 is a longitudinal sectional view of the image pickup unit 24 in accordance with a first embodiment of the present invention.

Arranged on the distal end of the image pickup unit 24 is a optical window member 31 which is a sapphire lens having a concave surface and exposed to the external surface of the insert section. The concave lens has a flat surface on the distal end surface thereof (the bottom surface) while having a concave surface on the proximal end surface thereof. The optical window member 31 has a metal coating on the outer circumference thereof, and is soldered in an air-tight manner to a first metal lens barrel 32 that has been plated for soldering. The metal coating includes three layers of coating of chromium (Cr), nickel (Ni), and gold (Au), for example, which are film-formed using deposition, sputtering and plating techniques. The first lens barrel 32 is preferably fabricated of a stainless steel such as SUS 304 or SUS303. Stainless steel is less expensive than other special metals. Since a stainless steel structure, even with a thin thickness, still presents a sufficient mechanical strength, the image pickup unit is reduced in size. Furthermore, since stainless steel is corrosion resistant, the endoscope 1 is not corroded in the autoclave sterilization process. The pre-soldering plating of the first lens barrel 32 may be any of gold plating, nickel plating, or tin plating, for example. These platings present high wettability to a brazing material such as solder, and are highly glossy. The pre-soldering plating process typically results in a glossy surface.

The pre-soldering plating process is performed on the inner circumference of the first lens barrel 32. If the pre-soldering plating process is performed on the edge chamfer of the distal end of the first lens barrel 32 and a mating portion of the optical window member 31, a good air-tightness is assured. No plating is applied on the outer circumference of the first lens barrel 32 on the distal end portion thereof. In this arrangement, no solder flows over the outer circumference of the first lens barrel 32 during a soldering operation. The image pickup unit 24 is thus prevented from enlarging in the outer diameter on the distal end portion thereof, and a failure in the assembly of the image pickup unit 24 into the distal end body 21 is thus avoided. The outer circumference of the image pickup unit 24 is masked during the plating operation or the plating may be peeled off during a secondary process.

A second metal lens barrel 34 having a low-reflectance surface is inserted into and fixed in the first lens barrel 32. The second lens barrel 34 houses at least a portion of an optical member forming an objective lens system 22 except the optical window. At least a distal end surface 38 of the second lens barrel 34 is subjected to a black surface treatment process for a low-reflectance surface, such as chromic oxide deposition, black chromium plating, or black copper plating. Among other platings, a black chromium plating and black copper plating offer particularly high anti-reflection capability because of high blackness thereof, and involve a low cost. Since the second lens barrel 34 is arranged in a location from which a light beam is most likely reflected, the distal end surface 38, namely, a light-incident front surface, has preferably a black surface finish having a low-reflectance feature for controlling light reflection therefrom. The second lens barrel 34 is preferably fabricated of the same material as that of the first lens barrel 32, and is thus preferably fabricated of stainless steel for the same reason applicable to the first lens barrel 32.

The second lens barrel 34 may be subjected to the black surface low-reflection finish on the inner circumference thereof in addition to the distal end surface 38 thereof.

The first lens barrel 32 is inserted into the inner circumference of an image pickup barrel 37. The two barrels 32 and 37 are air-tight bonded to each other using laser welding. Designated 33 is a laser weld portion.

In this arrangement, the first lens barrel 32, the second lens barrel 34, and the image pickup barrel 37 thus form a triple-barrel structure.

Since the image pickup unit 24 has a step portion 36, the image pickup unit 24 is tentatively fixed onto the image pickup barrel 37 using an adhesive 35 after the two barrels are focus adjusted. After that, the two barrels are laser welded to each for air-tightness.

A single objective lens unit includes the first lens barrel 32, the optical window member 31, the second lens barrel 34, and the optical members forming the objective optical system 22 supported by the second lens barrel 34. Arranged on the proximal end of the objective lens unit is the image pickup device 23 as the image pickup means.

The image pickup device 23 is bonded to a cover glass 46 using a light-transmissive optical adhesive. The cover glass 46 in turn is bonded to the image pickup barrel 37 using an adhesive. Specifically, the image pickup device 23 is supported by the image pickup barrel 37 through the cover glass 46. An infrared cutoff filter is interposed between the image pickup device 23 and the cover glass 46.

An adhesive 48 having a low vapor penetrant feature fills space around the image pickup device 23, and a metallic reinforcement barrel 49 covers the adhesive 48. A heat-shrinking tube 50 covers the outer circumference of the reinforcement barrel 49. The reinforcement barrel 49 is bonded to the image pickup barrel 37 using an adhesive. In this arrangement, no vapor for the autoclave sterilization process is in direct contact with the image pickup device 23, and the image pickup device 23 is not degraded in the course of the autoclave sterilization process. The heat shrinking tube 50 insulates almost all portion of the housing of the image pickup unit 24.

The image pickup device 23 includes a TAB (Tape Automated Bonding) member 51. The TAB member 51 is electrically connected to a cable 52. The heat shrinking tube 50 covers the cable 52 on the outer circumference thereof. A string 53 reliably fastens the heat shrinking tube 50 onto the cable 52.

The first lens barrel 32 and the second lens barrel 34 are bonded to each other on the mating portions thereof using an adhesive, and the image pickup barrel 37 and the cover glass 46 are bonded to each other on the mating portions thereof using an adhesive. An adhesive having a high resistance to a high-pressure and high-temperature vapor and a high gas barrier feature is used there. The adhesive used here is robust and free from serious degradation such as cracks unless the adhesive is directly attacked by a high-pressure and high-temperature vapor.

The present embodiment may be modified as described below. Such a modification is equally applicable to an embodiment to be discussed later.

The image pickup means may be an image guide fiber.

The optical window may be formed of an optical material having a resistance to a high-temperature and high-pressure vapor, other than sapphire.

Soldering may be brazing. Soldering here is included into the brazing.

The black surface finish may be one of black nickel plating, a black surface finish based on a technique other than plating, and any other black surface finish.

The first lens barrel may be fabricated of a metal having a good brazing bond, thereby requiring no particular surface treatment for brazing. For example, a copper alloy containing a large copper content, such as brass or monel, a nickel ally containing a large nickel content, or Kovar may be used. Since these materials are subject to corrosion, they need to be protected by any means so that these materials are not directly exposed to the vapor in the autoclave sterilization. An alloy, such as monel, containing a large nickel content, is expensive, but is resistant to corrosion and has a sufficient mechanical strength. When one of these materials is used for the first lens barrel of the present invention, a pre-brazing surface treatment process is advantageously eliminated.

The embodiment of the present invention has been discussed. The endoscope 1 thus constructed is used for medical purposes. After use, the endoscope 1 is put into a chamber of an autoclave sterilization apparatus. In the autoclave sterilization process, the chamber is filled with a high-temperature and high-pressure vapor.

Since the concave lens, as the optical window member 31, exposed to the external surface of the endoscope 1, is air-tight connected using soldering or the like, no vapor enters through the mating portions of the concave lens and the first lens barrel 32.

The vapor may enter into the endoscope 1 through the adhesive and a member fabricated of the polymeric material. Since the endoscope 1 includes the check valve, a large amount of vapor is not positively admitted into the endoscope 1. The internal components are not exposed to the vapor under a high pressure of 0.2 Mpa. The mating portions of the image pickup unit 24 not exposed to the external surface, i.e., the mating portions of the first lens barrel 32 and the second lens barrel 34, the mating portions of the second lens barrel 34 and the image pickup barrel 37, and the mating portions of the image pickup barrel 37 and the cover glass 46 are free from a direct attack by the vapor under the high pressure in the autoclave sterilization process. If the mating portions are manufactured of an adhesive having a resistance to high temperature and high pressure and a high gas barrier feature, vapor sufficient enough to cause cloud in the field of view in the objective optical system is not admitted into the endoscope 1.

In this embodiment, the first lens barrel 32, the second lens barrel 34, and the image pickup barrel 37 are all manufactured of metals and have almost equal thermal expansion coefficients, and preferably are manufactured of the same metal and have an equal thermal expansion coefficient. Under a temperature change in the autoclave sterilization process, the components are less subject to stress therebetween. In other words, the mating portions of the adhesive are resistant to peeling. Since the filler 27 fills space around the image pickup unit 24, almost no vapor reaches the above-mentioned mating portions. Furthermore, the filler 27 is preferably manufactured of a material having a resistance to high temperature and high pressure and a high gas barrier feature.

The autoclave sterilization process is typically followed by a drying process. In the drying process, the chamber is depressurized, moisture sticking to the endoscope 1 in the course of the sterilization process is removed, and the chamber is dried. Since the check valve arranged in the endoscope 1 is opened, moisture and vapor introduced into the endoscope 1 are removed, and the interior of the endoscope 1 is then also dried. A small amount of vapor may enter the endoscope 1 and be accumulated there in each sterilization process, and vapor may finally penetrate into the objective optical system through the mating portions of the adhesive, thereby causing a cloud on the lens system inside. Such a trouble is readily precluded.

It is extremely difficult to perform two types of surface treatments, i.e., the pre-brazing plating process and the black surface treatment process, on limited localized areas of a small lens barrel in the endoscope 1. This embodiment results in a structure that generates neither cloud nor optical problems such as flare in the viewing optical system in the autoclave sterilization process.

The endoscope 1 permits an instrument to pass through a channel (not shown) to perform a high-frequency treatment. The distal end portion of the distal end body 21 of the endoscope 1 is covered with the distal end cover 28 fabricated of an insulator material. The distal end portion 8 is thus insulated from outside. Even if the second lens barrel 34 is manufactured of a metal rather than an insulator material such as a ceramic, the high-frequency treatment can also be performed.

The present embodiment provides the following advantages.

With this embodiment, neither cloud nor optical problems such as flare are generated in the viewing optical system during the autoclave sterilization process. The black low-reflectance surface finish is applied not only on the distal end surface of the second lens barrel 34, namely, the light-incident front surface, but also on the inner circumference of the second lens barrel 34. The generation of the optical problems such as flare is effectively controlled.

The second lens barrel 34 is manufactured of a metal with the distal end surface thereof subjected to the non-glossy black surface treatment process for low reflectance such as the black chromium plating or the black copper plating. The generation of the optical problems such as flare is thus reliably controlled.

Given the same machinability and mechanical strength, the second lens barrel 34 manufactured of the metal becomes thinner in structure than that manufactured of a ceramic or a plastic. The image pickup unit is thus reduced in size.

The first lens barrel 32, the second lens barrel 34, and the image pickup barrel 37 are all manufactured of metals and have almost equal thermal expansion coefficients, or preferably are manufactured of the same metal and have an equal thermal expansion coefficient. The components are less subject to stress occurring therebetween. The mating portions in the endoscope 1, even formed of the adhesive, are less subject to cracks through which vapor could penetrate.

The inner circumference of the second lens barrel 34 may be subjected to a matte surface process for an irregular reflection surface rather than the black low-reflectance surface treatment process.

A second embodiment of the present invention is discussed hereinafter.

Figure 5:
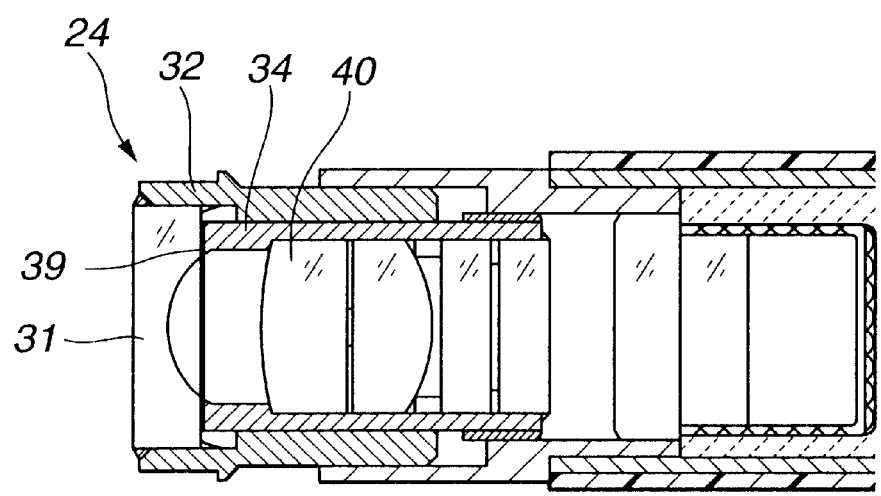
FIG. 5 is a longitudinal sectional view of an image pickup unit in accordance with a second embodiment of the present invention.

The second embodiment is identical to the first embodiment with a portion thereof modified, and is discussed referring to FIG. 5. The discussion that follows focuses on only the difference therebetween. Like elements are identified with like reference numerals, and the discussion thereof is skipped here.

In the second embodiment, an optical diaphragm member 39 is arranged in alignment and glued on the distal end face of the second lens barrel 34 using an adhesive or the like as shown in FIG. 5. With the optical diaphragm member 39 in contact with the optical window member 31, the first lens barrel 32 and the second lens barrel 34 are bonded to each other.

At least the light-incident front surface, namely, the distal end surface of the optical diaphragm member 39 is subjected to the non-glossy black surface treatment process for the black low-reflectance feature, such as the black chromium plating or the black copper plating. Like the first embodiment, the second embodiment equally controls the generation of flare.

In the second embodiment, the optical diaphragm member 39 is assembled beforehand in the vicinity of the distal end of the second lens barrel 34 or the distal end of an optical member 40 supported by the second lens barrel 34 at the distal end portion thereof. The assembly of the image pickup unit 24 is as easy as that of the first embodiment.

Instead of assembling beforehand the optical diaphragm member 39 on the distal end of the second lens barrel 34, the optical diaphragm member 39 may be glued in alignment onto the proximal end surface of the optical window member 31 which is already bonded to the first lens barrel 32, and the second lens barrel 34 is then inserted into the first lens barrel 32.

The proximal end surface or the side surface of the optical window member 31 may be subjected to a black surface treatment process to form a doughnut-shaped coating. The doughnut-shaped surface finish portion forms a diaphragm member having a low-reflectance feature.

Since the diaphragm has a low-reflectance property, the generation of flare is controlled only by subjecting the inner circumference of the second lens barrel 34 to the black low-reflectance surface treatment process or the irregular reflection surface treatment process.

The second embodiment provides the same advantages as those of the first embodiment.

Figure 6:
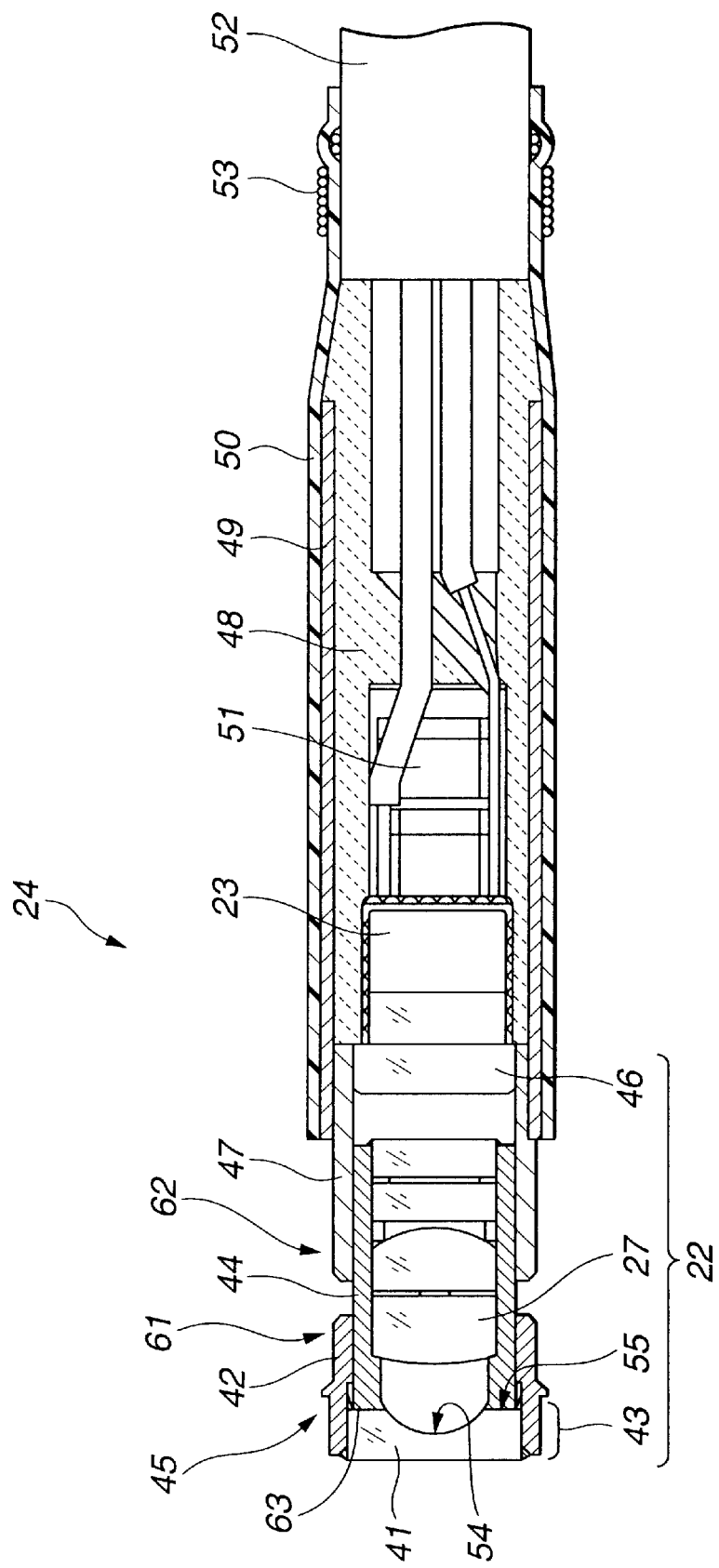
FIG. 6 is a longitudinal sectional view of an image pickup unit in accordance with third through seventh embodiments of the present invention.

A third embodiment of the present invention is discussed below. FIG. 6 is a longitudinal sectional view of the image pickup unit 24 in accordance with the third embodiment of the present invention.

The image pickup unit 24 includes on the distal end thereof an optical window member 41, namely, a concave lens fabricated of sapphire and exposed to the external surface of the insert section. The optical window member 41, having a metal coating on the outer circumference thereof, is air-tight bonded to a pre-soldering plated, first metal lens barrel 42 through soldering. The metal coating is formed of three layers of chromium (Cr), nickel (Ni), and gold (Au), and is film-formed using deposition, sputtering, plating, and other techniques. The first lens barrel 42 is preferably fabricated of a stainless steel such as SUS 304 or SUS303. Stainless steel is less expensive than other special metals. Since a stainless steel structure, even with a thin thickness, still presents a sufficient mechanical strength, the image pickup unit is reduced in size. Furthermore, since stainless steel is corrosion resistant, the endoscope 1 is not corroded in the autoclave sterilization process. The pre-soldering plating of the first lens barrel 42 may be any of gold plating, nickel plating, or tin plating, for example. These platings present high wettability to a brazing material such as solder, and are highly glossy. The pre-soldering plating process typically results in a glossy surface.

The pre-soldering plating process is performed on the inner circumference of the first lens barrel 42. If the pre-soldering plating process is performed on at least the edge chamfer of the distal end of the first lens barrel 42 and a mating portion of the optical window member 41, a good air-tightness is assured. No plating is applied on the outer circumference 43 of the first lens barrel 42 on the distal end portion thereof. In this arrangement, no solder flows over the outer circumference of the first lens barrel 42 during a soldering operation. The image pickup unit 24 is thus prevented from enlarging in the outer diameter on the distal end portion thereof, and a failure in the assembly of the image pickup unit 24 into the distal end body 21 is thus avoided. The outer circumference of the image pickup unit 24 is masked during the plating operation or the plating may be peeled off during a secondary process.

A second metal lens barrel 44 having a low-reflectance surface is inserted into and fixed in the first lens barrel 42 in the inner circumference thereof. The second lens barrel 44 houses at least a portion of an optical member forming an objective lens system 22 except the optical window. At least the inner circumference and a distal end surface 63 of the second lens barrel 44 is subjected to a non-glossy black surface treatment process for a low-reflectance surface, such as chromic oxide deposition, black chromium plating, or black copper plating. Among other platings, a black chromium plating and black copper plating offer particularly high anti-reflection capability because of high blackness thereof, and involve a low cost. Since the second lens barrel 44 is arranged in a location from which a light beam is most likely reflected, the second lens barrel 44 has preferably a surface finish that is not only less glossy but also reliably light-reflective with the black low-reflectance surface finish. The second lens barrel 44 is preferably fabricated of the same material as that of the first lens barrel 42, and is thus preferably fabricated of stainless steel for the same reason applicable to the first lens barrel 42.

The inner circumference of the second lens barrel 44 may be subjected to a matte surface treatment process for an irregular reflection surface.

A single objective lens unit 45 includes the first lens barrel 42, the optical window member 41, the second lens barrel 44, and the optical members forming the objective optical system 22 supported by the second lens barrel 44. Arranged on the proximal end of the objective lens unit 45 is the image pickup device 23 as the image pickup means.

The image pickup device 23 is bonded to a cover glass 46 using a light-transmissive optical adhesive. The cover glass 46 in turn is bonded to the image pickup barrel 47 using an adhesive. Specifically, the image pickup device 23 is supported by the image pickup barrel 47 through the cover glass 46. The objective lens unit 45 is inserted into the image pickup barrel 47, and focus adjustment is performed by adjusting the relative position of the image pickup device 23 with respect to the objective lens unit 45 during assembly. Subsequent to the focus adjustment, the second lens barrel 44 is bonded to the image pickup barrel 47 using an adhesive. The image pickup barrel 47 is preferably manufactured of a metal, and is more preferably manufactured of the same material as that of the second lens barrel 44. Like the second lens barrel 44, the image pickup barrel 47 is preferably subjected to the black low-reflectance surface treatment process. An infrared cutoff filter is interposed between the image pickup device 23 and the cover glass 46.

An adhesive 48 having a low vapor penetrant feature fills space around the image pickup device 23, and a metallic reinforcement barrel 49 covers the adhesive 48. A heat-shrinking tube 50 covers the outer circumference of the reinforcement barrel 49. The reinforcement barrel 49 is bonded to the image pickup barrel 47 using an adhesive. In this arrangement, no vapor for the autoclave sterilization process is in direct contact with the image pickup device 23, and the image pickup device 23 is not degraded in the course of the autoclave sterilization process. The heat shrinking tube 50 insulates almost all portion of the housing of the image pickup unit 24.

The image pickup device 23 includes a TAB (Tape Automated Bonding) member 51. The TAB member 51 is electrically connected to a cable 52. The heat shrinking tube 50 covers the cable 52 on the outer circumference thereof. A string 53 reliably fastens the heat shrinking tube 50 onto the cable 52.

The first lens barrel 42 and the second lens barrel 44 are bonded to each other on the mating portions thereof using the adhesive, the second lens barrel 44 and the image pickup barrel 47 are bonded to each other on the mating portions thereof using the adhesive, and the image pickup barrel 47 and the cover glass 46 are bonded to each other on the mating portions thereof using the adhesive. An adhesive having a high resistance to a high-pressure and high-temperature vapor and a high gas barrier feature is used there. The adhesive used here is robust and free from serious degradation such as cracks unless the adhesive is directly attacked by a high-pressure and high-temperature vapor.

The present embodiment may be modified as described below. Such a modification is equally applicable to all embodiments including the second embodiment.

The image pickup means may be an image guide fiber.

The optical window may be formed of an optical material having a resistance to a high-temperature and high-pressure vapor, other than sapphire.

Soldering may be brazing. Soldering is here included in the brazing.

The black surface finish may be one of black nickel plating, a black surface finish based on a technique other than plating, and any other black surface finish.

The first lens barrel 42 may be fabricated of a metal having a good brazing bond, thereby requiring no particular surface finish for brazing. For example, a copper alloy containing a large copper content, such as brass or monel, a nickel ally containing a large nickel content, or Kovar may be used. Since these materials are subject to corrosion, they need to be protected by any means so that these materials are not directly exposed to the vapor in the autoclave sterilization. An alloy, such as monel, containing a large nickel content, is expensive, but is resistant to corrosion and has a sufficient mechanical strength. When one of these materials is used for the first lens barrel 42 of the present invention, a pre-brazing surface treatment process is advantageously eliminated.

The second embodiment of the present invention has been discussed. The endoscope 1 thus constructed is used for medical purposes. After use, the endoscope 1 is put into a chamber of an autoclave sterilization apparatus. In the autoclave sterilization process, the chamber is filled with a high-temperature and high-pressure vapor.

Since the concave lens, as the optical window member 41, exposed to the external surface of the endoscope 1, is air-tight bonded using soldering or the like, no vapor enters through the mating portions of the concave lens and the first lens barrel 42.

The vapor may enter into the endoscope 1 through the adhesive and a member fabricated of the polymeric material. Since the endoscope 1 includes the check valve, a large amount of vapor is not positively admitted into the endoscope 1. The internal components are not exposed to the vapor under a high pressure of 0.2 Mpa. The mating portions of the image pickup unit 24 not exposed to the external surface, i.e., the mating portions of the first lens barrel 42 and the second lens barrel 44, the mating portions of the second lens barrel 44 and the image pickup barrel 47, and the mating portions of the image pickup barrel 47 and the cover glass 46 are free from a direct attack by the vapor under the high pressure in the autoclave sterilization process. If the mating portions are manufactured of an adhesive having a resistance to high temperature and high pressure and a high gas barrier feature, vapor sufficient enough to cause cloud in the objective optical system is not admitted into the endoscope 1.

In this embodiment, the first lens barrel 42, the second lens barrel 44, and the image pickup barrel 47 are all manufactured of metals and have almost equal thermal expansion coefficients, and preferably are manufactured of the same metal and have an equal thermal expansion coefficient. Under a temperature change in the autoclave sterilization process, the components are less subject to stress therebetween. In other words, the mating portions of the adhesive are resistant to peeling. Since the filler 27 fills space around the image pickup unit 24, almost no vapor reaches the above-mentioned mating portions. Furthermore, the filler 27 is preferably manufactured of a material having a resistance to high temperature and high pressure and a high gas barrier feature.

The autoclave sterilization process is typically followed by a drying process. In the drying process, the chamber is depressurized, moisture sticking to the endoscope 1 in the course of the sterilization process is removed, and the chamber is dried. Since the check valve arranged in the endoscope 1 is opened, moisture and vapor introduced into the endoscope 1 are removed, and the interior of the endoscope 1 is then also dried. A small amount of vapor may enter the endoscope 1 and be accumulated there in each sterilization process, and vapor may finally penetrate into the objective optical system through the mating portions of the adhesive, thereby causing a cloud on the lens system inside. Such a trouble is readily precluded.

Subsequent to the autoclave sterilization process, the endoscope 1 is used again to observe the body cavity and the internal portion of the body of a human. The surface of the second lens barrel 44 supporting the optical members forming the objective optical system 22 is subjected to the black surface treatment process for low reflectance property such as the black chromium plating or the black copper plating. The inner circumference of the first lens barrel 42 is almost hidden with the second lens barrel 44 inserted thereinto. This arrangement controls the generation of the optical problems such as flare arising from reflections from the brazed surface of the first lens barrel 42, thereby permitting a good observation through the endoscope 1.

It is extremely difficult to perform two types of surface finishes, i.e., the pre-brazing plating process and the black surface treatment process, on limited localized areas of a small lens barrel in the endoscope 1. This embodiment results in a structure that generates neither cloud nor optical problems such as flare in the viewing optical system in the autoclave sterilization process.

The endoscope 1 permits an instrument to pass through a channel (not shown) to perform a high-frequency treatment. The distal end portion of the distal end body 21 of the endoscope 1 is covered with the distal end cover 28 fabricated of an insulator material. The distal end portion 8 is thus insulated from outside. Even if the second lens barrel 44 is manufactured of a metal rather than an insulator material such as a ceramic, the high-frequency treatment can also be performed.

The present embodiment provides the following advantages.

This arrangement prevents clouding from being generated in the viewing optical system in the course of the autoclave sterilization and the optical problems such as the flare.

The second lens barrel 44 is manufactured of a metal, and the distal end surface, namely, the front light incident surface, and the inner circumference of the second lens barrel 44 are subjected to the non-glossy black surface treatment process for low reflectance such as the black chromium plating or the black copper plating. The generation of the optical problems such as the flare is thus reliably controlled.

The inner circumference of the second lens barrel 44 may be subjected to a matte surface treatment process for an irregular reflection surface.

Given the same machinability and mechanical strength, the second lens barrel 44 manufactured of the metal becomes thinner in structure than that manufactured of a ceramic or a plastic. The image pickup unit is thus reduced in size.

The second lens barrel 44 having the black low-reflectance surface is inserted into and fixed in the inner circumference of the first lens barrel 42 having surface plated for brazing. The single objective lens unit is formed of the first lens barrel 42, the optical window member, the second lens barrel 44, and the optical members supported by the second lens barrel 44. This arrangement prevents the field of view from being clouded and the flare from being generated while assuring the ease of assembly at the same level as that of a conventional image pickup unit. In this arrangement, as in the conventional image pickup unit, the objective lens unit 45 is inserted into the image pickup barrel 47 until focus is adjusted. When the focus adjustment is completed, the image pickup barrel 47 is fixed to the objective lens unit 45, thereby completing the image pickup unit. The ease of assembly is thus attained.

The first lens barrel 42 is inserted into and fixed in the second lens barrel 44, and the second lens barrel 44 is inserted into and fixed in the image pickup barrel 47. The image pickup unit is thus reduced in size.

During the assembly of the image pickup unit, the optical window member 41 and the first lens barrel 42, exposed to the external surface of the endoscope 1, are air-tight bonded to each other on the mating portions thereof using brazing such as soldering, and the other mating portions not exposed to the external surface of the endoscope 1 are bonded using the adhesive. This arrangement not only reduces the endoscope 1 in size but also assures the ease of assembly thereof. Since the endoscope 1 includes the check valve, a large amount of vapor is not positively admitted into the endoscope 1. This arrangement prevents the field of view from being clouded.

The first lens barrel 42, the second lens barrel 44, and the image pickup barrel 47 are all manufactured of metals and have almost equal thermal expansion coefficients, and preferably are manufactured of the same metal and have an equal thermal expansion coefficient. Under a temperature change in the autoclave sterilization process, the components are less subject to stress therebetween. The mating portions in the endoscope 1, even formed of the adhesive, are less subject to cracks through which vapor could penetrate.

A fourth embodiment of the present invention will now be discussed.

The fourth embodiment is identical to the third embodiment with a portion thereof modified, and is discussed with reference to FIG. 6. The discussion that follows focuses on only the difference therebetween. Like elements are identified with like reference numerals, and the discussion thereof is skipped here.

In the fourth embodiment, the first lens barrel 42 is air-tight bonded to the second lens barrel 44 using laser welding rather than an adhesive. The rest of the fourth embodiment remains unchanged from the third embodiment.

Since the mating portion of the image pickup unit not exposed to but closest to the external surface of the endoscope 1 is air-tight bonded in this arrangement, the probability that the field of view is clouded is more reduced than in the third embodiment.

Both the first lens barrel 42 and the second lens barrel 44 are manufactured of a metal, the laser welding permits the two barrels 42 and 44 to be easily air-tight bonded without increasing the diameter of the image pickup unit.

The first lens barrel 42 and the second lens barrel 44 are manufactured of the same material appropriate for use in laser welding, such as a metal like SUS304 having low contents of sulfur, phosphorus, carbon, etc.

Each of the first lens barrel 42 and the second lens barrel 44, except a laser weld portion 61 to be laser welded, is plated. If the laser weld portion 61 is plated, the gloss of the plate reflects a laser light beam, and a difference in melting point between the material of the barrel and the plate impedes a reliable air-tight bond in the laser welding operation. Therefore, weld portions to be laser welded, namely, the inner and outer circumferences of the first lens barrel 42 and the outer circumference of the second lens barrel 44 in the laser weld portion 61 are left unplated.

The present invention is not limited to the laser welding. The mating portions in this embodiment may be air-tight bonded using the brazing. However, since the metals are bonded, the laser welding free from fluxes is preferable.

The fourth embodiment has the following advantages.

Although an increase in the air-tight bond area increases the degree of difficulty with which the endoscope 1 is assembled, the probability that the field of view is clouded becomes lower in the fourth embodiment than in the third embodiment.

The first lens barrel 42 and the second lens barrel 44 are manufactured of metals, preferably of the same material. The two barrels 42 and 44 are thus easily air-tight bonded to each other. A structure less subject to clouding in the field of view is easily accomplished.

A fifth embodiment of the present invention will be discussed below.

The fifth embodiment is identical to the fourth embodiment with a portion thereof modified, and is discussed with reference to FIG. 6. The discussion that follows focuses on only the difference therebetween. The rest of the fifth embodiment remains unchanged from the fourth embodiment, and the discussion thereof is skipped here.

In the fifth embodiment, the second lens barrel 44 is air-tight bonded to the image pickup barrel 47 using laser welding or brazing. The rest of the fifth embodiment remains unchanged from the fourth embodiment. A laser weld portion 62 is shown in FIG. 6. This arrangement prevents vapor from penetrating into the objective optical system. The probability that the field of view is clouded becomes lower in the fifth embodiment than in the fourth embodiment.

The fifth embodiment has the following advantages.

Although an increase in the air-tight bond area increases the degree of difficulty with which the endoscope 1 is assembled, the probability that the field of view is clouded becomes lower in the fifth embodiment than in the fourth embodiment. The fifth embodiment provides the advantages of the third and fourth embodiments.

The second lens barrel 44 and the image pickup barrel 47 are manufactured of metals, preferably of the same material. The two barrels 42 and 47 are thus easily air-tight bonded. A structure less subject to clouding in the field of view is easily accomplished.

A sixth embodiment of the present invention will be discussed below.

The six embodiment is identical to the fifth embodiment with a portion thereof modified, and is discussed with reference to FIG. 6. The discussion that follows focuses on only the difference therebetween. The rest of the sixth embodiment remains unchanged from the fifth embodiment, and the discussion thereof is skipped here.

In the sixth embodiment, the image pickup barrel 47 is air-tight bonded to the cover glass 46 using laser welding or brazing. The rest of the sixth embodiment remains unchanged from the fifth embodiment.

In this arrangement, the objective optical system 22 is fully closed in an air-tight state and no clouding occurs in the field of view under any autoclave sterilization conditions.

The sixth embodiment has the following advantages.

Although an increase in the air-tight bond area increases the degree of difficulty with which the endoscope 1 is assembled, the probability that the field of view is clouded becomes lower in the sixth embodiment than in the fifth embodiment, and no clouding occurs in the field of view under any autoclave sterilization conditions. The sixth embodiment also provides the advantages of the third and fifth embodiment.

A seventh embodiment of the present invention will now be discussed.

The seventh embodiment is identical to the third through the sixth embodiment with a portion thereof modified, and is discussed with reference to FIG. 6. The discussion that follows focuses on only the difference therebetween. The rest of the seventh embodiment remains unchanged from that already discussed in connection with the third through sixth embodiments, and the discussion thereof is skipped here.

In the seventh embodiment, the second lens barrel 44 is manufactured of a black material rather than a metal. In this embodiment, the second lens barrel 44 is manufactured of black alumina which is a black ceramic. The black alumina has a high gas barrier property, thereby allowing almost no vapor to penetrate therethrough. The material is black in color, and has a light reflectance lower than that of a gray material such as sialon or silicon carbide. The black alumina has also a light blocking property. The black alumina is thus a ceramic appropriate for use in the lens barrel in the autoclave sterilization type endoscope 1. Since the material itself is black, no black surface finish is required.

Since the black alumina has an insulating property, it works as an insulating barrel. A high-frequency operation is possible in the structure in which the metallic distal end body 21 is exposed to the distal end portion 8 of the endoscope 1 without the distal end cover 28 fabricated of an insulator material shown in FIG. 3.

When the second lens barrel 44 and the first lens barrel 42 are air-tight bonded to each other or when the second lens barrel 44 and the image pickup barrel 47 are air-tight bonded to each other, as in the fourth and fifth embodiments, a metal to ceramic bonding needs to be performed. In this case, a special bonding technique as disclosed in Japanese Unexamined Patent Application Publication No. 2000-287913 is thus used, for example.

In the seventh embodiment, the second lens barrel 44 is fabricated of the black alumina. Alternatively, other black material may be used. The black material may be black ceramics or black polymeric materials. The black polymeric materials include a polymeric material that is obtained by blackening each of polyetheretherketone, polyphenylsulfone, polyphenylene sulfide, and polysulfone. These materials are less expensive than the ceramics. When one of these materials is used, the filler 27 is applied as shown in FIG. 3 to assure gas barrier so that vapor entering the endoscope 1 does not reach the surface of the second lens barrel 44. Like the ceramic, these materials need no black surface finish because the surface thereof is already black.

The seventh embodiment has the following advantages.

In addition to the advantages of the third embodiment, the high-frequency operation is possible even in the structure in which the metal is exposed to the external surface of the endoscope 1.

Since the material itself forming the second lens barrel 44 is black, the seventh embodiment present the same advantages as those of the third embodiment without the black surface treatment process.

An eighth embodiment of the present invention is discussed below.

The eighth embodiment is identical to each the third through seventh modifications with a portion thereof modified, and is discussed with reference to FIG. 7. The discussion that follows focuses on only the difference therebetween. The rest of the eighth embodiment remains unchanged from the third through seventh embodiments, and the discussion thereof is skipped here.

Figure 7:
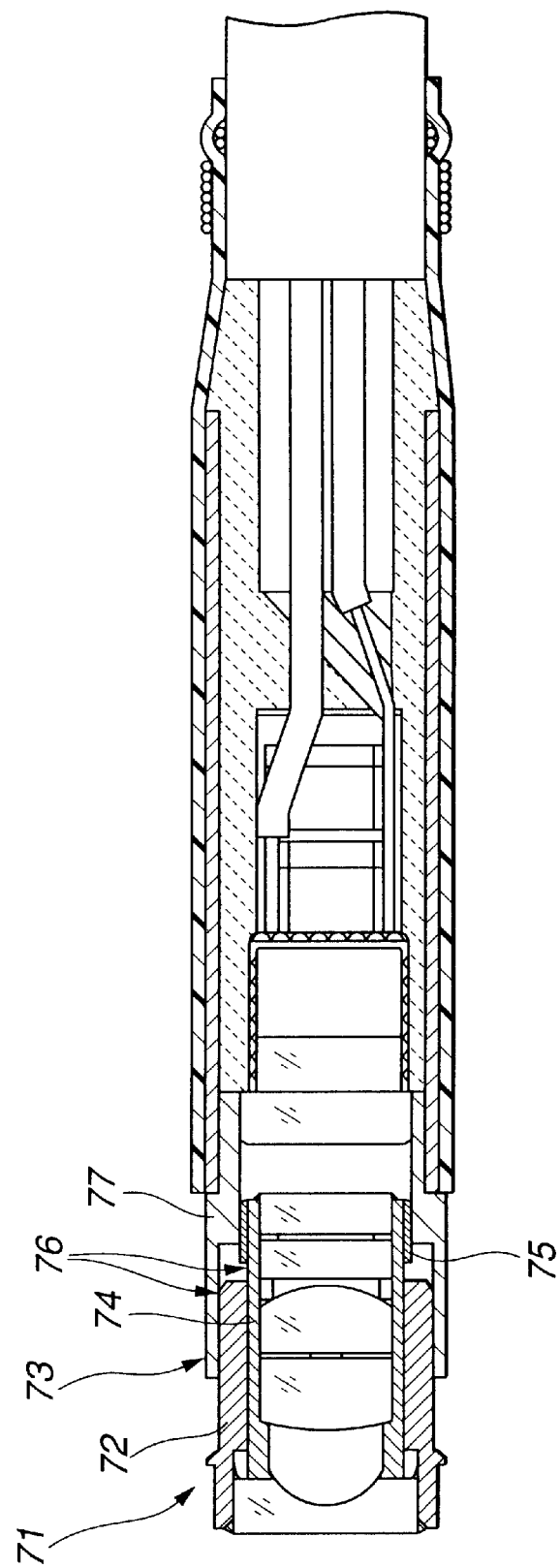
FIG. 7 is a longitudinal sectional view of an image pickup unit in accordance with an eighth embodiment of the present invention.

FIG. 7 is a longitudinal sectional view of an image pickup unit in accordance with the eighth embodiment of the present invention. In the eighth embodiment, a first lens barrel 72 is inserted into and fixed in the inner circumference of an image pickup barrel 77, and the two barrels 72 and 77 are laser welded for air-tightness. FIG. 7 shows a laser weld portion 73. A second lens barrel 74 housing an objective lens group is housed in the first lens barrel 72.

In this arrangement, the number of air-tight mating portions is reduced by one in comparison with the third through seventh embodiments. The ease of assembly is thus improved. A triple barrel structure is thus formed of the first lens barrel 72, the second lens barrel 74, and the image pickup barrel 77.

Since an objective lens unit 71 is provided with a step portion 76, the image pickup barrel 77 is tentatively fixed to the objective lens unit 71 using an adhesive 75 after focus adjustment. The image pickup barrel 77 is then laser welded to the objective lens unit 71 for air-tightness.

In the above discussion, the laser welding is used to connect the first lens barrel 72 to the image pickup barrel 77. If the two barrels are metals, the air-tight bonding is performed as described in connection with the fourth embodiment. If the two barrels are a combination of the metal and ceramic, the air-tight bonding is performed as described in connection with the seventh embodiment.

Generally, if an adhesive is present within a laser weld portion, the adhesive becomes carbonized, thereby causing a poor air-tight bond. In the above-referenced fifth embodiment, the laser welding needs to be performed without tentatively connecting the image pickup barrel 47 to the objective lens unit 45 using the adhesive. In contrast, the eighth embodiment is free from this limitation. The ease of assembly is thus improved.

The eighth embodiment has the following advantages.

In the eighth embodiment, the number of air-tight mating portions is reduced by one in comparison with the third through seventh embodiments. The ease of assembly is thus improved. The eighth embodiment provides the advantages of the third through seventh embodiments.

In the course of the autoclave sterilization process, no clouding is generated in the viewing optical system and no optical problems such as the flare are generated. The optical problems such as the flare are more effectively controlled by performing the black low-reflectance surface treatment process on not only the distal end surface, namely, the front light incident surface, of the second lens barrel 74 but also the inner circumference of the second lens barrel 74.

The second lens barrel 74 is manufactured of a metal, and a non-glossy black surface treatment process for very low reflectance, such as the black chromium plating or the black copper plating, is performed on the distal end surface of the second lens barrel 74. In this way, a structure that is less subject to the optical problems such as the flare is produced.

Given the same machinability and mechanical strength, the second lens barrel 74 manufactured of the metal becomes thinner in structure than that manufactured of a ceramic or a plastic. The image pickup unit is thus reduced in size.

The first lens barrel 72, the second lens barrel 74, and the image pickup barrel 77 are all manufactured of metals and have almost equal thermal expansion coefficients, and preferably are manufactured of the same metal and have an equal thermal expansion coefficient. The components are less subject to stress therebetween. The mating portions in the endoscope 1, even formed of the adhesive, are less subject to cracks through which vapor could penetrate.

The inner circumference of the second lens barrel 74 may be subjected to a matte surface process for an irregular reflection surface rather than the black low-reflectance surface treatment process.

A ninth embodiment of the present invention is discussed below.

The ninth embodiment is identical to the eighth embodiment with a portion thereof modified, and is discussed with reference to FIG. 8. The discussion that follows focuses on only the difference therebetween. The rest of the ninth embodiment remains unchanged from the eighth embodiment, and the discussion thereof is skipped here.

Figure 8:
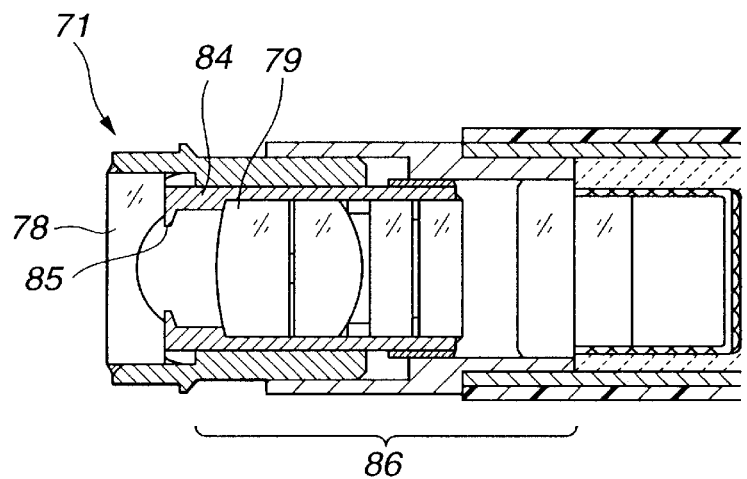
FIG. 8 is a longitudinal sectional view of an image pickup unit in accordance with a ninth embodiment of the present invention.

FIG. 8 is a longitudinal sectional view of an image pickup unit in accordance with the ninth embodiment of the present invention. In the ninth embodiment, an optical diaphragm member 85 is formed at the distal end of a second lens barrel 84 having a black low-reflectance surface. Also, the optical diaphragm member 85 has a black low-reflectance surface. The optical diaphragm member 85 is interposed between an optical window member 78 and a distal end optical member 79 supported by the second lens barrel 84.

Since no additional light rays are input to an objective optical system 86 arranged to be proximal with respect to the optical window member 78 in the ninth embodiment, the ninth embodiment provides a structure that is less subject to the optical problems such as the flare than the third embodiment.

The generation of the flare is more controlled by performing a black low-reflectance surface treatment or an irregular reflection surface treatment on the inner circumference of the second lens barrel 84.

The ninth embodiment provides the following advantages.

In addition to the advantages of the third embodiment, the ninth embodiment results in a structure that is less subject to the optical problems such as the flare than the third embodiment.

Two lens barrels, namely, the first lens barrel and the second lens barrel 84, are separately formed, and the optical diaphragm member 85 is arranged at the distal end of the first lens barrel. Even in the structure that the optical window member 78 is soldered to the lens barrel, the optical diaphragm member 85 having a diaphragm function is easily formed between the optical window member 78 and the distal end optical member 79 supported by the second lens barrel 84.

A tenth embodiment of the present invention is discussed below.

The tenth embodiment is identical to the ninth embodiment with a portion thereof modified, and is discussed with reference to FIG. 9. Discussed below is a difference therebetween and the rest of the tenth embodiment is identical to the ninth embodiment. The discussion thereof is thus skipped here.

Figure 9:
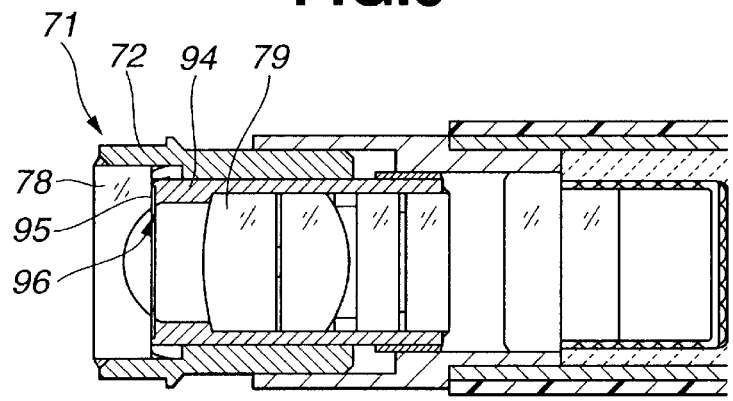
FIG. 9 is a longitudinal sectional view of an image pickup unit in accordance with a tenth embodiment of the present invention.

FIG. 9 is a longitudinal sectional view of an image pickup unit in accordance with the tenth embodiment of the present invention. An optical diaphragm 95 is arranged at the distal end of a second lens barrel 94 in the ninth embodiment as shown in FIG. 9. Specifically, the optical diaphragm 95 is arranged between an optical window member 78 and a distal end optical member 79 supported by the second lens barrel 94. The ease of assembly of an objective lens unit 71 is assured as in the embodiments shown in FIGS. 6 and 7 by attaching beforehand the optical diaphragm member 95 to the second lens barrel 94.

Two lens barrels, namely, the first lens barrel 72 and the second lens barrel 94, are separately formed. Even in the structure that the optical window member 78 is soldered to the first lens barrel 72, the optical diaphragm member 95 is easily arranged between the optical window member 78 and the distal end optical member 79 supported by the second lens barrel 94.

The optical diaphragm member 95 is preferably fabricated of a very thin material. With the thin material employed, the area 96 of the optical diaphragm 95 in parallel with the optical axis becomes minimal, and the amount of quantity of light reflected from the area 96 is smaller than that in the ninth embodiment. The probability that the flare is generated is thus smaller than in the ninth embodiment.

The optical diaphragm member 95 is produced by photoetching a phosphor bronze sheet to a desired shape, and then performing the black copper surface treatment process to the photoetched phosphor bronze sheet. Alternatively, the optical diaphragm member 95 is produced by electro-forming a nickel sheet, and by performing the black chromium process on the electro-formed nickel sheet. The optical diaphragm member 95 is thus a member having a thin, black low-reflectance surface. These materials have typically a thickness of 0.03 mm.

Even when a member thicker than the phosphor bronze sheet is used, the member can perform the function of an optical diaphragm member as long as a material having a black low-reflectance surface is deposited thereon.

The generation of the flare is controlled by subjecting the inner circumference of the second lens barrel 94 to the black low-resistance surface treatment process or the irregular reflection surface treatment process.

The tenth embodiment has the following advantages.

In addition to the advantages of the third and ninth embodiments, the tenth embodiment is less subject to the optical problems such as the flare than the ninth embodiment.

Two lens barrels, namely, the first lens barrel 72 and the second lens barrel 94, are separately formed. Even in the structure that the optical window member 78 is soldered to the first lens barrel 72, the optical diaphragm member 95 is easily arranged between the optical window member 78 and the distal end optical member 79 supported by the second lens barrel 94.

Several modifications of the optical diaphragm member are discussed below.

A variety of arrangements of the optical diaphragm member is contemplated as shown in FIGS. 10 through 15. FIGS. 10 through 15 are longitudinal sectional views illustrating first through sixth arrangement examples of the optical diaphragm in the image pickup unit of the present invention.

Figure 10:
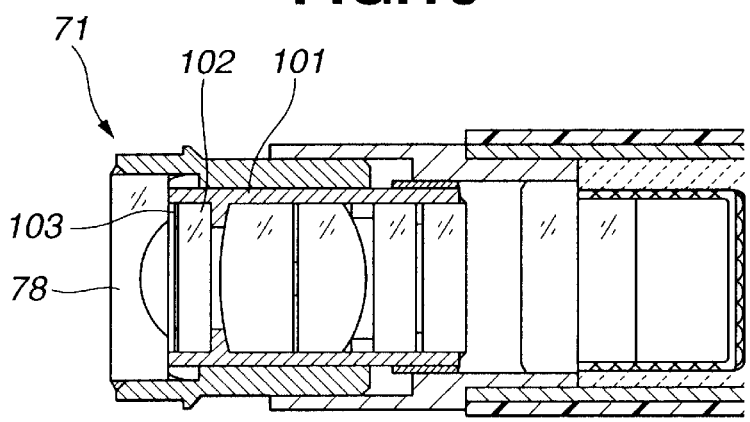
FIG. 10 is a longitudinal sectional view illustrating a first arrangement of an optical diaphragm in the image pickup unit of the present invention.

Referring to FIG. 10, an optical diaphragm member 103 is bonded to the end face of a distal end optical member 102 supported by a second lens barrel 101.

Figure 11:
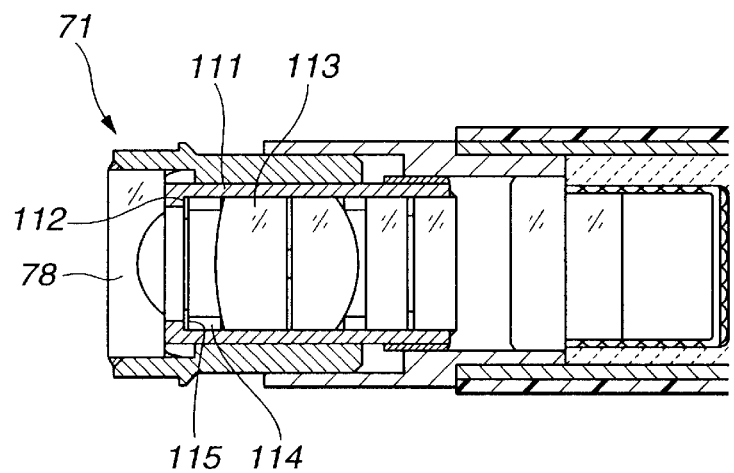
FIG. 11 is a longitudinal sectional view illustrating a second arrangement of the optical diaphragm in the image pickup unit of the present invention.

Referring to FIG. 11, an abutment face 112 is formed at the end of a second lens barrel 111. An optical diaphragm member 115 is clamped between the abutment face 112 and an optical member 113 through a spacer ring 114. The spacer ring 114 is a metal member which has been subjected to the black surface treatment process.

Figure 12:
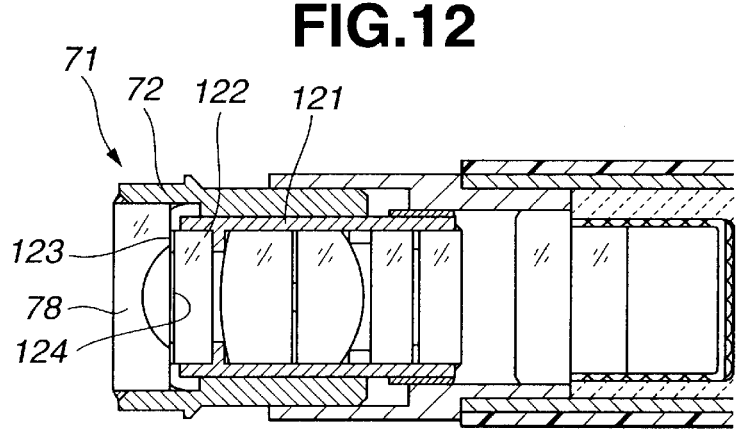
FIG. 12 is a longitudinal sectional view illustrating a third arrangement of the optical diaphragm in the image pickup unit of the present invention.

Referring to FIG. 12, an optical diaphragm member 123 is bonded in alignment to the end face of a distal end optical member 122 supported by a second lens barrel 121 using an adhesive. With the optical diaphragm member 123 in contact with the optical window member 78, the first lens barrel 72 and the second lens barrel 121 are bonded to each other.

Figure 13:
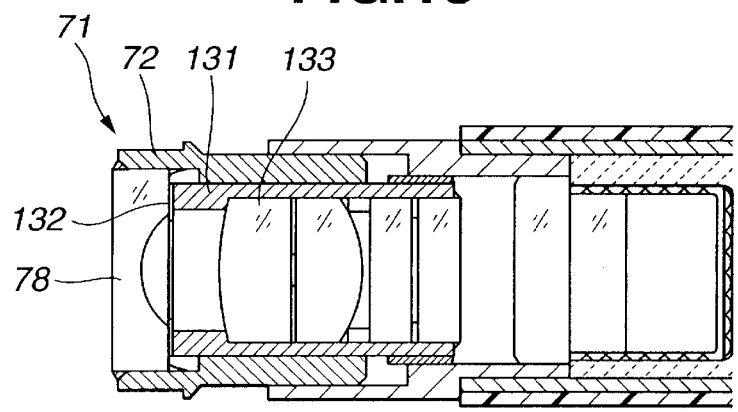
FIG. 13 is a longitudinal sectional view illustrating a fourth arrangement of the optical diaphragm in the image pickup unit of the present invention.

Referring to FIG. 13, an optical diaphragm member 132 is bonded in alignment to the end face of a second lens barrel 131 using an adhesive. With the optical diaphragm member 132 in contact with the optical window member 78, the first lens barrel 72 and the second lens barrel 131 are bonded to each other.

In this arrangement, the optical diaphragm member 132 is mounted beforehand in the vicinity of the distal end surface of the second lens barrel 131 or to the distal end surface of a distal end optical member 133 supported by the second lens barrel 131. The ease of assembly of the objective lens unit 71 remains unchanged from the embodiments shown in FIGS. 6 and 7.

Instead of bonding beforehand the optical diaphragm member 132 to the distal end surface of the second lens barrel 131 as shown in FIG. 13, the optical diaphragm member 132 is bonded in alignment to the proximal end surface of the optical window member 78 connected to the first lens barrel 72, and then the second lens barrel 131 is inserted into the first lens barrel 72.

Figure 14:
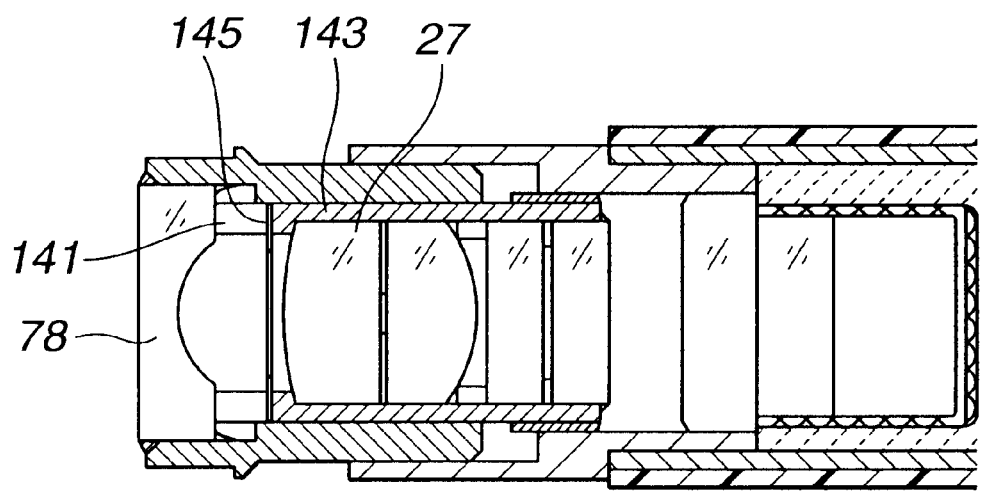
FIG. 14 is a longitudinal sectional view illustrating a fifth arrangement of the optical diaphragm in the image pickup unit of the present invention.
Figure 15:
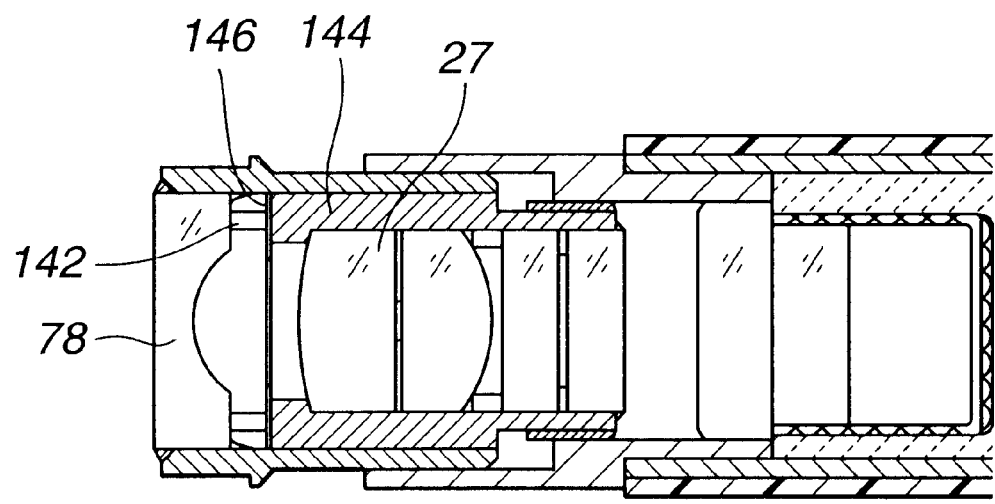
FIG. 15 is a longitudinal sectional view illustrating A sixth arrangement of the optical diaphragm in the image pickup unit of the present invention.

The optical diaphragm may also be arranged as shown in FIGS. 14 and 15. FIGS. 14 and 15 are longitudinal sectional views illustrating the arrangement of the optical diaphragm member in the image pickup unit of the present invention. Referring to FIG. 14, an optical diaphragm member 145 is clamped between an optical window member 78 and a second lens barrel 143 through a spacer ring 141. Referring to FIG. 15, an optical diaphragm member 146 is clamped between an optical window member 78 and a second lens barrel 144 through a spacer ring 142.

In comparison to the arrangements shown in FIGS. 9 through 13, the ease of assembly of the objective lens unit 71 is simple because the optical diaphragm members 145 and 146 are respectively bonded using the adhesive and because one assembly step is reduced.

The optical diaphragm member may be clamped between the distal end optical member supported by the second lens barrel and the optical window member.

Referring to FIG. 6, the proximal end surface or the side surface of the optical window member may be subjected to a black surface treatment process in a doughnut-shaped formation. The doughnut-shaped surface finish portion may be used as an optical diaphragm member. The black surface treatment process forms a three-layer structure of a chromium oxide film-chromium film-chromium oxide film. For example, a doughnut-shaped black surface treatment is performed on a surface 55 except a semispherical recess 54 on the distal end face of the optical window member.

Referring to FIG. 12, the optical diaphragm member 123 may be a doughnut-shaped black surface coated on the distal end surface 124 of the distal end optical member 122.

An eleventh embodiment of the present invention is discussed below.

The eleventh embodiment is identical to the eighth embodiment with a portion thereof modified, and is discussed with reference to FIG. 16. Discussed below is a difference therebetween and the rest of the eleventh embodiment is identical to the eighth embodiment. The discussion thereof is thus skipped here.

Figure 16:
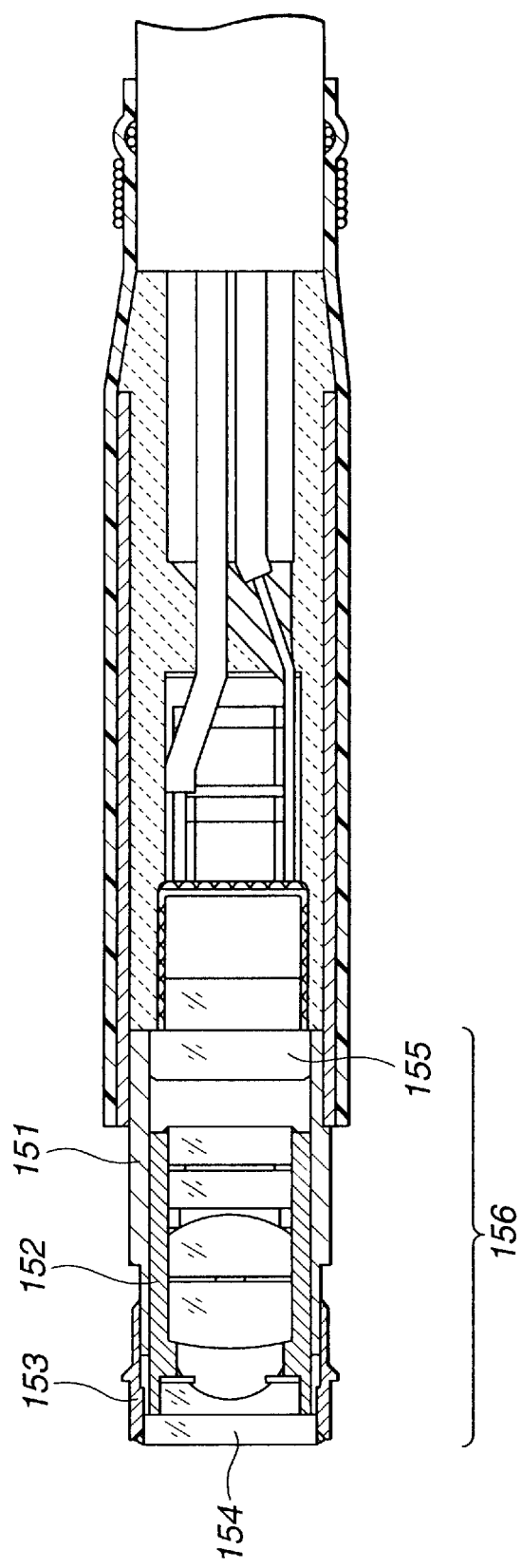
FIG. 16 is a longitudinal sectional view of an image pickup unit in accordance with an eleventh embodiment of the present invention.

FIG. 16 is a longitudinal sectional view of an image pickup unit in accordance with the eleventh embodiment of the present invention. The image pickup unit of the eleventh embodiment includes an image pickup barrel 151 fabricated of a metal, a second lens barrel 152 inserted into the image pickup barrel 151 within the inner circumference thereof and subjected to a black low-reflectance surface treatment process, and a first lens barrel 153 fitted over the image pickup barrel 151 around the outer circumference thereof and subjected to a pre-brazing surface treatment process. The inner circumference of the second lens barrel 152 may have an irregular reflection surface processed through a matte surface treatment process.

An optical window member 154 as a glass cover is air-tight bonded to the first lens barrel 153 through soldering. The image pickup barrel 151 and a cover glass 155 are also air-tight bonded to each other through soldering. The first lens barrel 153 and the image pickup barrel 151 are laser welded for air-tightness.

In an assembly process, the second lens barrel 152 supporting optical members forming an objective optical system 156 as a viewing optical system is inserted into the image pickup barrel 151 for focus adjustment. After focus adjustment, the two barrels are fixed using an adhesive. The first lens barrel 153 to which the optical window member 154 is air-tight bonded is fitted over the image pickup barrel 151 on the outer circumference thereof, and the first lens barrel 153 and the image pickup barrel 151 are air-tight bonded to each other.

The eleventh embodiment encapsulates the objective optical system as the same air-tight level as that of the eighth embodiment. No clouding is thus generated under any autoclave sterilization conditions. Like in the third embodiment, the eleventh embodiment is free from the optical problems such as the flare.

The image pickup unit has a three-barrel structure formed of the first lens barrel 153, the second lens barrel 152, and the image pickup barrel 151.

The present invention provides the following advantages.

In addition to the advantages of the third through seventh embodiments, the ease of assembly of the image pickup unit is improved because the eleventh embodiment has the number of the air-tight mating portions smaller than that of the third through seventh embodiment by one.

As discussed above, the present invention provides the endoscope which is free from clouding in the viewing optical system in the course of the autoclave sterilization process, and free from the optical problems such as the flare, and has a smaller diameter distal end portion.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least a distal end surface of one of the second lens barrel, a diaphragm member, a spacer ring, and the optical members has light reflectance lower than that of the metal-plated surface of the first lens barrel, wherein at least the inner circumference of the second lens barrel has light reflectance lower than that of the metal-plated surface of the first lens barrel or has a reflection surface more irregular than the metal-plated surface of the first lens barrel, and wherein the second lens barrel supporting the optical members and the first lens barrel supporting the optical window member are bonded to each other as a single lens unit with the second lens barrel mated into the inner circumference of the first lens barrel, and the lens unit is mated into and bonded to an image pickup barrel supporting image pickup, wherein the image pickup barrel comprises a cover glass, and wherein the cover glass and the image pickup barrel are air-tight bonded to each other.

2. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least a distal end surface of one of the second lens barrel, a diaphragm member, a spacer ring, and the optical members has light reflectance lower than that of the metal-plated surface of the first lens barrel, and wherein the second lens barrel and the first lens barrel are bonded to each other as a single lens unit with the second lens barrel mated into the inner circumference of the first lens barrel, and the lens unit is mated into and bonded to an image pickup barrel supporting image pickup, wherein the image pickup barrel comprises a cover glass, and wherein the cover glass and the image pickup barrel are air-tight bonded to each other.

3. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least a distal end surface of one of the second lens barrel, a diaphragm member, a spacer ring, and the optical members has light reflectance lower than that of the metal-plated surface of the first lens barrel, and wherein the second lens barrel and the first lens barrel are bonded to each other as a single lens unit with the second lens barrel mated into the inner circumference of the first lens barrel, and the lens unit is mated into and bonded to an image pickup barrel supporting image pickup, wherein the first lens barrel and the second lens barrel are bonded to each other by brazing or by laser welding, wherein the image pickup barrel and the lens unit are bonded to each other by brazing or by laser welding the image pickup barrel to the second lens barrel, wherein the image pickup barrel comprises a cover glass, and wherein the cover glass and the image pickup barrel are air-tight bonded to each other.

4. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least a distal end surface of one of the second lens barrel, a diaphragm member, a spacer ring, and the optical members has light reflectance lower than that of the metal-plated surface of the first lens barrel, and wherein the second lens barrel and the first lens barrel are bonded to each other as a single lens unit with the second lens barrel mated into the inner circumference of the first lens barrel, and the lens unit is mated into and bonded to an image pickup barrel supporting image pickup, wherein the first lens barrel and the second lens barrel are bonded to each other by brazing or by laser welding, wherein the image pickup barrel and the lens unit are bonded to each other by one of brazing and laser welding the image pickup barrel to the first lens barrel.

5. An endoscope according to claim 4, wherein the first lens barrel of the lens unit is fitted into the inner circumference of the image pickup barrel.

6. An endoscope according to claim 4, wherein the first lens barrel of the lens unit is fitted over the outer circumference of the image pickup barrel.

7. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least the inner circumference of the second lens barrel has light reflectance lower than that of the metal-plated surface of the first lens barrel or has a reflection surface more irregular than the metal-plated surface of the first lens barrel, and wherein the second lens barrel and the first lens barrel are bonded to each other as a single lens unit with the second lens barrel mated into the inner circumference of the first lens barrel, and the lens unit is mated into and bonded to an image pickup barrel supporting image pickup, wherein the image pickup barrel comprises a cover glass, and wherein the cover glass and the image pickup barrel are air-tight bonded to each other.

8. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least the inner circumference of the second lens barrel has light reflectance lower than that of the metal-plated surface of the first lens barrel or has a reflection surface more irregular than the metal-plated surface of the first lens barrel, and wherein the second lens barrel and the first lens barrel are bonded to each other as a single lens unit with the second lens barrel mated into the inner circumference of the first lens barrel, and the lens unit is mated into and bonded to an image pickup barrel supporting image pickup, wherein the first lens barrel and the second lens barrel are bonded to each other by brazing or by laser welding, wherein the image pickup barrel and the lens unit are bonded to each other by brazing or by laser welding the image pickup barrel to the second lens barrel, wherein the image pickup barrel comprises a cover glass, and wherein the cover glass and the image pickup barrel are air-tight bonded to each other.

9. An endoscope comprising:

a viewing optical system including a plurality of optical members and an optical window member, the optical window member having a metal coating on an outer circumference thereof, a first lens barrel having a metal-plated surface at a distal portion thereof, the metal-plated surface being coupled with the outer circumference of the optical window member in an air-tight manner by one of brazing and soldering, and a second lens barrel supporting the optical members on an inner circumference thereof, and coupled with the first lens barrel such that light from the optical window member is incident on the optical members, wherein at least the inner circumference of the second lens barrel has light reflectance lower than that of the metal-plated surface of the first lens barrel or has a reflection surface more irregular than the metal-plated surface of the first lens barrel, and wherein the second lens barrel and the first lens barrel are bonded to each other as a single lens unit with the second lens barrel mated into the inner circumference of the first lens barrel, and the lens unit is mated into and bonded to an image pickup barrel supporting image pickup, wherein the first lens barrel and the second lens barrel are bonded to each other by brazing or by laser welding, wherein the image pickup barrel and the lens unit are bonded to each other by one of brazing and laser welding the image pickup barrel to the first lens barrel.

10. An endoscope according to claim 9, wherein the first lens barrel of the lens unit is fitted into the inner circumference of the image pickup barrel.

11. An endoscope according to claim 9, wherein the first lens barrel of the lens unit is fitted over the outer circumference of the image pickup barrel.

* * * * *